(12) United States Patent
First

(10) Patent No.: US 7,465,458 B2
(45) Date of Patent: Dec. 16, 2008

(54) METHODS FOR TREATING EYE DISORDERS

(75) Inventor: Eric R. First, Boston, MA (US)

(73) Assignee: Allergan, Inc., Irvine, CA (US)

( * ) Notice: Subject to any disclaimer, the term of this patent is extended or adjusted under 35 U.S.C. 154(b) by 102 days.

(21) Appl. No.: 11/737,641

(22) Filed: Apr. 19, 2007

(65) Prior Publication Data

US 2008/0199498 A1 Aug. 21, 2008

Related U.S. Application Data

(63) Continuation of application No. 10/442,590, filed on May 20, 2003, now Pat. No. 7,220,422.

(51) Int. Cl.
*A61K 39/08* (2006.01)
*A61F 2/00* (2006.01)
*A01N 43/56* (2006.01)

(52) U.S. Cl. .................... 424/247.1; 424/423; 514/406; 604/511; 604/531

(58) Field of Classification Search ........................ None
See application file for complete search history.

(56) References Cited

U.S. PATENT DOCUMENTS

| | | | |
|---|---|---|---|
| 5,250,293 A * | 10/1993 | Gleich | 424/78.04 |
| 5,401,243 A * | 3/1995 | Borodic | 604/511 |
| 5,437,291 A | 8/1995 | Pasricha et al. | |
| 5,616,122 A * | 4/1997 | Lam et al. | 604/521 |
| 5,670,484 A | 9/1997 | Binder | |
| 5,714,468 A | 2/1998 | Binder | |
| 5,766,605 A | 6/1998 | Sanders et al. | |
| 5,989,545 A | 11/1999 | Foster et al. | |
| 6,063,768 A * | 5/2000 | First | 514/14 |
| 6,113,915 A | 9/2000 | Aoki et al. | |
| 6,139,845 A | 10/2000 | Donovan | |
| 6,143,306 A | 11/2000 | Donovan | |
| 6,265,379 B1 | 7/2001 | Donovan | |
| 6,299,893 B1 | 10/2001 | Schwartz et al. | |
| 6,306,403 B1 | 10/2001 | Donovan | |
| 6,306,423 B1 * | 10/2001 | Donovan et al. | 424/423 |
| 6,312,708 B1 | 11/2001 | Donovan | |
| 6,328,977 B1 | 12/2001 | Donovan | |
| 6,358,513 B1 | 3/2002 | Voet et al. | |
| 6,358,926 B2 | 3/2002 | Donovan | |
| 6,365,164 B1 | 4/2002 | Schmidt | |
| 6,383,509 B1 | 5/2002 | Donovan | |
| 6,395,277 B1 | 5/2002 | Graham | |
| 6,423,319 B1 | 7/2002 | Brooks et al. | |
| 6,429,189 B1 | 8/2002 | Borodic | |
| 6,440,964 B1 | 8/2002 | Cagle et al. | |
| 6,458,365 B1 | 10/2002 | Aoki et al. | |
| 6,464,986 B1 | 10/2002 | Aoki et al. | |
| 6,585,993 B2 * | 7/2003 | Donovan et al. | 424/423 |
| 6,692,481 B2 * | 2/2004 | Guerrero | 604/521 |
| 6,743,424 B1 * | 6/2004 | Donovan | 424/94.5 |
| 7,211,261 B1 * | 5/2007 | Moyer et al. | 424/236.1 |
| 7,220,422 B2 * | 5/2007 | First | 424/247.1 |
| 7,390,496 B2 * | 6/2008 | Ackerman | 424/247.1 |
| 7,393,537 B2 * | 7/2008 | Ackerman | 424/247.1 |
| 2002/0064536 A1 * | 5/2002 | Hunt | 424/247.1 |
| 2002/0192239 A1 | 12/2002 | Borodic | |
| 2003/0092640 A1 * | 5/2003 | Boettner | 514/28 |
| 2003/0114830 A1 * | 6/2003 | Guerrero | 604/521 |
| 2004/0058313 A1 * | 3/2004 | Abreu | 435/5 |
| 2004/0122254 A1 | 6/2004 | Fujimoto et al. | |
| 2004/0170665 A1 | 9/2004 | Donovan | |
| 2004/0204471 A1 * | 10/2004 | Seibert | 514/406 |
| 2004/0213811 A1 * | 10/2004 | Ackerman | 424/239.1 |
| 2004/0220100 A1 | 11/2004 | Waugh | |
| 2004/0265935 A1 | 12/2004 | Atassi | |
| 2005/0025778 A1 * | 2/2005 | Cormier et al. | 424/185.1 |
| 2005/0043410 A1 | 2/2005 | Brazzell et al. | |
| 2006/0067950 A1 | 3/2006 | Taylor | |
| 2006/0106104 A1 | 5/2006 | Vehige | |
| 2006/0182767 A1 | 8/2006 | Borodic | |

(Continued)

FOREIGN PATENT DOCUMENTS

EP 1 147 776 A2 10/2001

(Continued)

OTHER PUBLICATIONS

Bigalke, H. et al.; Botulinum A Neurotoxin Inhibits Non-Cholinergic Synaptic Transmission in Mouse Spinal Cord Neurons in Culture; *Brain Research*; 360; 318-324; 1985.

(Continued)

*Primary Examiner*—Mark Navarro
*Assistant Examiner*—Ginny Portner
(74) *Attorney, Agent, or Firm*—Claude L. Nassif; Stephen Donovan; Martin Voet

(57) ABSTRACT

The present invention provides methods of treating an eye disorder. The methods comprise a step of locally administering a *Clostridial* toxin to the eye of a patient to treat the disorder. The eye disorder may be associated with an inflammation of the eye, including for example, bacterial conjunctivitis, fungal conjunctivitis, viral conjunctivitis, uveitis, keratic precipitates, macular edema, and inflammation response after intra-ocular lens implantation. The *Clostridial* toxin may be produced by a *Clostridial beratti*, a *Clostridia butyricum*, a *Clostridial tetani* bacterium and/or a *Clostridial botulinum*.

11 Claims, No Drawings

U.S. PATENT DOCUMENTS

2006/0182783 A1* 8/2006 Hughes et al. ............... 424/427
2006/0211752 A1 9/2006 Kohn
2007/0059336 A1* 3/2007 Hughes et al. ............... 424/426

FOREIGN PATENT DOCUMENTS

WO          WO01/01959 A1     1/2001

OTHER PUBLICATIONS

Bigalke, H. et al.; *Tetanus Toxin and Botulinum A Toxin Inhibit Release and Uptake of Various Transmitters, as Studied with Particulate Preparations from Rat Brain and Spinal Cord*; Naunyn-Schmiedeberg's Arch Pharmacol; 316; 244-251, 1981.

Binz, T. et al.; *The Complete Sequence of Botulinum Neurotoxin Type A and Comparison with other Clostridial Neurotoxins; J Biological Chemistry* 265 (16); 9153-9158; 1990.

Cohen, D.A.,et al., *Botulinum injection therapy for blepharospasm: a review and report of 75 patients*, Clinical Neuropharmacology, vol. 9, No. 5, pp. 415-429 1986 Raven Press, NY.

Denniston, A et al., Hop. Med, Aug. 2001, vol. 62(6), pp. 477-479.

Duggan, Michael J. et al., *A survey of botulinum neurotoxin substrate expression in cells*; Mov Disord; May 1995; 10(3) p. 376.

Ellis, MF et al., *An evealuation of the safety and efficacy of botulinum toxin type A (BOTOX) when used to produce a protective ptosis*, Clin and Exper Ophthalmology, Dec. 2001, vol. 29(6), pp. 394-399.

Ferrari et al.; *The protein disulphide-isomerase family: unraveling a string of folds*; Journal Biochem (1999) 339; 1-10.

Habermann, E. et al.; *Tetanus Toxin and Botulinum A and C Neurotoxins Inhibit Noradrenaline Release From Cultured Mouse Brain*; J. Neurochem; 51(2) 522-527; 1988.

Habermann, E.; Inhibition by Tetanus and Botulinum A Toxin of the release of [3H]GABA from Rat Brain Homogenate; *Experientia*; 44; 224-226; 1988.

Habermann; E.; I-Labeled Neurotoxin from Clostridium Botulinum A: Preparation, Binding to Synaptosomes and Ascent to the Spinal Cord; *Naunyn-Schmiedeberg's Arch. Pharmacol*; 281; 1974; 47-56.

Horwath-Winter et al.; *The Effect of Botulinum Toxin A Treatment on Tear Function Parameters and on the Ocular Surface; Adv Exp Med Biol*; 2002; 506 (Pt B); 1241-6.

Jankovic, J. et al.; *Therapy with Botulinum Toxin*; Marcel Dekker, Inc., 1994; p. 5.

Marjama-Jyons, J. et al.; *Tremor-Predominant Parkinson's Disease; Drug & Aging* 16(4); 273-278; 2000.

Moyer, E. et al.; *Botulinum Toxin Type B: Experimental and Cllinical Experience*, Chapter 6, pp. 71-85 of *Therapy With Botulinum Toxin*, edited by Jankovic, J. et al. 1994, Marcel Dekker, Inc.

Naumann et al.; *Botulinum toxin type A in the treatment of focal, axiallary and palmar hyperhidrosis and other hyperhidrotic conditions; European J. Neurology* 6 (Supp 4); S111-S1150; 1999.

Ophthalmology Times, *World of Ophthalmology Converges Upon New Orleans*, V23, No. 21, p. 40.

Pearce, L.B.; *Pharmacologic Characterization of Botulinum Toxin for Basic Science and Medicine; Toxicon*; 35(9) 1373-1412 at 1393.

Ragona et al.; *Management of Parotid Sialocele with Botulinum Toxin; Laryngoscope* 109; 1344-1346; 1999.

Sanchez-Prieto, J. et al.; *Botulinum Toxin A Blocks Glutamate Exocytosis from Guinea Pg Cerebral Cortical Synaptosomes; Eur J Biochem*; 165; 675-681; 1987.

Schantz, E.J. et al.; *Properties and use of Botulinum Toxin and other Microbial Neurotoxins in Medicine; Microbiol Rev*; 56; 80-99; 1992.

Singh; *Critical Aspects of BacterialProtein Toxins*; pp. 63-84 Chapter 4 of *Natural Toxins II*, edited by B.R. Singh et al., Plenum Press, New York 1976.

Sloop et al.; *Reconstituted Botulinum toxin type A does not lose potency in humans if it is refrozen or refrigerated for 2 weeks before use; Neurology*; 48; 249-53; 1997.

Soylev, MF et al., *Anesthesia with EMLA cream for botulinum A toxin injection into eyelids*, Ophthalmologica, vol. 216, 2002, pp. 356-358.

Tran et al.; *Calcitonin Gene-Related Peptide Induces IL-8 Synthesis in Human Corneal Epithelial Cells; The Journal of Immunology*; Apr. 15, 2000; 164(8); 4307-12.

Uddin, J.M., *Treatment of upper eyelid retraction associated with thyroid eye disease with subconjunctival botulinum toxin injection*, Ophthalmology Jun. 2002, No. 6, vol. 109, pp. 1183-1187.

Weigand et al.; Naunyn-Schmiedeberg's Arch Pharmacol; 1976; 292, 161-165.

* cited by examiner ing eye disorders and to compositions comprising a *Clostridium* toxin for treating said disorders. In particular, the methods are related to treating eye disorders associated with inflammation.

METHODS FOR TREATING EYE DISORDERS

CROSS-REFERENCE TO RELATED APPLICATIONS

This application is a continuation of prior application Ser. No. 10/442,590, filed May 20, 2003, the disclosure of which is herein incorporated by reference in its entirety.

FIELD OF THE INVENTION

The present invention relates to methods for treating eye disorders and to compositions comprising a *Clostridium* toxin for treating said disorders. In particular, the methods are related to treating eye disorders associated with inflammation.

BACKGROUND OF THE INVENTION

Inflammation, or reddening, of the superficial tissues of the eye is a relatively common affliction. Eye disorders associated with inflammation include, for example, bacterial conjunctivitis, fungal conjunctivitis, viral conjunctivitis, uveitis, keratic precipitates, macular edema, and inflammation response after intra-ocular lens implantation.

Various types of palliative treatments have been used to treat this condition. The most common treatment includes the administration of eye drops which contain emollients and other ingredients designed to ease the discomfort due to the inflammation and to eliminate the redness associated with the condition. These treatments, however, have not been entirely satisfactory, however.

For example, current treatments often involve frequent applications of a medicinal eye drop. Unfortunately, however, many commercially available eye drops include preservatives, an ingredient that may be quite harmful to the eye. As such, frequent application of the commercially available eye drops may not be healthy for the eye.

Thus, there is a continued need to have improved methods and compositions for treating eye disorders. The present invention provides such compositions and methods for treating eye disorders. In particular, the methods and compositions of the present invention involve the use of a *Clostridium* toxin.

The present invention is, in part, based upon a surprising discovery that a *Clostridial* toxin may be administered to an eye of a patient, e.g., a mammal, to treat eye disorders.

A *Clostridial* toxin that is commonly used clinically to treat various muscular conditions is botulinum toxin. For example, botulinum toxins have been used in clinical settings for the treatment of neuromuscular disorders characterized by hyperactive skeletal muscles. In 1989 a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Additionally, intramuscular botulinum toxin has been used in the treatment of tremor in patients with Parkinson's disease, although it has been reported that results have not been impressive. Marjama-Jyons, J., et al., *Tremor-Predominant Parkinson's Disease*, Drugs & Aging 16(4); 273-278:2000.

In addition to having pharmacologic actions at the peripheral location, botulinum toxins may also have inhibitory effects in the central nervous system. Work by Weigand et al, *Naunyn-Schmiedeberg's Arch. Pharmacol.* 1976; 292, 161-165, and Habermann, *Naunyn-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

A botulinum toxin has also been proposed for the treatment of rhinorrhea, hyperhydrosis and other disorders mediated by the autonomic nervous system (U.S. Pat. No. 5,766,605), tension headache, (U.S. Pat. No. 6,458,365), migraine headache (U.S. Pat. No. 5,714,468), post-operative pain and visceral pain (U.S. Pat. No. 6,464,986), pain treatment by intraspinal toxin administration (U.S. Pat. No. 6,113,915), Parkinson's disease and other diseases with a motor disorder component, by intracranial toxin administration (U.S. Pat.

No. 6,306,403), hair growth and hair retention (U.S. Pat. No. 6,299,893), psoriasis and dermatitis (U.S. Pat. No. 5,670,484), injured muscles (U.S. Pat. No. 6,423,319, various cancers (U.S. Pat. No. 6,139,845), pancreatic disorders (U.S. Pat. No. 6,143,306), smooth muscle disorders (U.S. Pat. No. 5,437,291, including injection of a botulinum toxin into the upper and lower esophageal, pyloric and anal sphincters)), prostate disorders (U.S. Pat. No. 6,365,164), inflammation, arthritis and gout (U.S. Pat. No. 6,063,768), juvenile cerebral palsy (U.S. Pat. No. 6,395,277), inner ear disorders (U.S. Pat. No. 6,265,379), thyroid disorders (U.S. Pat. No. 6,358,513), parathyroid disorders (U.S. Pat. No. 6,328,977). Additionally, controlled release toxin implants are known (see e.g. U.S. Pat. Nos. 6,306,423 and 6,312,708).

SUMMARY OF THE INVENTION

The present invention provides for methods of treating an eye disorder. The methods comprise a step of locally administering a *Clostridial* toxin to the eye of a mammal to treat the disorder. In some embodiments, the methods comprise a step of locally administering a *Clostridial* toxin to a cornea of a mammal to treat the disorder. For example, a *Clostridial* toxin may be administered topically to the cornea to treat the eye disorder. In some embodiments, the *Clostridial* toxin is administered with a vasoconstrictor.

Further in accordance with the present invention, the eye disorder is associated with an inflammation of the eye. Examples of eye disorders associated with an inflammation include, but are not limited to, bacterial conjunctivitis, fungal conjunctivitis, viral conjunctivitis, uveitis, keratic precipitates, macular edema, and inflammation response after intra-ocular lens implantation.

The present invention provides for compositions that may be employed for treating an eye disorder. In accordance with the present invention, the compositions comprise an ophthalmically acceptable carrier, a *Clostridial* toxin in an amount effective to treat an eye disorder when the composition is administered to an eye, and a polyanionic component in an amount effective to provide lubrication to an eye when the composition is administered to an eye. In some embodiments, the composition is a solution. In some embodiments, the *Clostridial* toxin may be a toxin produced by a *Clostridial beratti*, a *Clostridia butyricum*, a *Clostridial tetani* bacterium or a *Clostridial botulinum*. In some embodiments, the *Clostridial* toxin may be a botulinum toxin type A, B, $C_1$, D, E, F, G and/or mixtures thereof. In some embodiments, the *Clostridial* toxin is a botulinum toxin type A. In some embodiments, the polyanionic component comprises an anionic cellulosic derivative (e.g., carboxy methyl celluloses). In some embodiments, the compositions further comprise a vasoconstrictor.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION OF THE INVENTION

The present invention is directed to treating an eye disorder by administering a *Clostridial* toxin to the eye of a mammal. A "mammal" as used herein includes, for example, humans, rats, rabbits, mice and dogs. Any of the *Clostridial* toxin s or compositions described below can be used in the methods described herein.

In some embodiments, the eye disorder is associated with an inflammation of the eye. Examples of eye disorders associated with an inflammation include, but are not limited to, bacterial conjunctivitis, fungal conjunctivitis, viral conjunctivitis, uveitis, keratic precipitates, macular edema, and inflammation response after intra-ocular lens implantation.

Without limiting the invention to any theory or mechanism of operation, it is believed that an eye inflammation, for example inflammation of the cornea, is due in part to the release of a Calcitonin Gene-Related Peptide (CGRP). For example, neutrophil infiltration of the clear corneal surface is a hallmark of corneal inflammation in the human eye. Tran et al. showed that CGRP, a neuropeptide known to be released from the termini of corneal sensory, can bind to human corneal epithelial cells (HCEC) and induce expression of the neutrophil chemotactic protein IL-8. *J. Immunol.* 2000 Apr. 15; 164(8):4307-12.

Specifically, Tran et al. demonstrated the following: HCEC bound CGRP in a saturable manner with a Kd of $2.0\times10-9$ M. Exposure of HCEC to CGRP induced a significant increase in intracellular cAMP levels and enhanced IL-8 synthesis nearly 4-fold. Also, the capacity of CGRP to stimulate cAMP and IL-8 synthesis was abrogated in the presence of the CGRP receptor antagonist CGRP8-37. CGRP stimulation had no effect on the half-life of IL-8 mRNA while increasing IL-8 pre-mRNA synthesis more than two fold. Moreover, CGRP did not induce monocyte chemotactic protein-1 or RANTES synthesis, nor did the neuropeptide enhance detectable increases in steady state levels of mRNA specific for these two beta-chemokines. Based on that result, Tran et al. suggest that HCEC possess CGRP receptors capable of initiating a signal transduction cascade that differentially activates expression of the IL-8 gene but not the genes for monocyte chemotactic protein-1 or RANTES. Furthermore, Tran et al. concluded that the capacity of CGRP to stimulate IL-8 synthesis in HCEC shows that sensory neurons are involved in induction of acute inflammation at the eye surface.

Also, without wishing to limit the invention to any theory or mechanism of operation, it is believed that inhibiting the release of CGRP from sensory neurons in the eye may be effective in treating inflammation, preferably acute inflammation, of the eye. It is further believed that CGRP within a neuron is packaged in vesicles, and the inhibition of release of these vesicles may prevent the release of CGRP from the nerve terminals. *Clostridial* toxin may be effectively employed in inhibiting the release of CGRP from the nerve terminals in the eye.

In some embodiments, a *Clostridial* toxin is locally administered to the eye to treat the eye disorder. The *Clostridial* toxin may be locally administered to the cornea of the eye. In one embodiment, the *Clostridial* toxin is administered topically to treat the eye disorder. For example, the *Clostridial* toxin may be administered topically to the cornea of the eye.

In some embodiments, a botulinum toxin type A is locally administered to the eye to treat an eye disorder that is associated with an inflammation. In some embodiments, the botulinum toxin type A is administered to the cornea of the eye. In some embodiments a botulinum toxin type A is administered topically to an eye to treat an eye disorder that is associated with an inflammation. For example, a botulinum toxin type A may be administered topically to the cornea of the eye to treat an eye disorder associated with an inflammation, wherein the eye disorders may include bacterial conjunctivitis, fungal conjunctivitis, viral conjunctivitis, uveitis, keratic precipitates, macular edema, and/or inflammation response after intra-ocular lens implantation.

In some embodiments, the *Clostridial* toxin is administered with a vasoconstrictor to treat the eye disorder. Examples of vasoconstrictors are tetrahydrozoline, ephedrine, naphazoline, phenylephrine, and/or mixtures thereof. The vasoconstrictor may be administered with the *Clostridial* toxin in a composition, as described below, or may be administered separately before or after the toxin.

The methods of treatment herein advantageously allow for the disordered (afflicted) eye to be treated with a reduced amount of preservatives coming into contact with the eye. For example, the *Clostridial* toxin that is administered to the eye according to this invention may or may not be associated with a preservative. The *Clostridial* toxin is associated with a preservative when, for example, the toxin is one of the ingredients in an ophthalmic composition having preservatives. However, the administration of these compositions to the eye for effective treatment may be less frequent, as compared to the frequency of administration of an existing commercial eye formulation. Because the present composition is administered less frequently than commercially available eye formulations to achieve the same therapeutic effect, less preservatives come into contact with the eye when the composition of the present invention is administered.

Of course, an ordinarily skilled medical provider can determine the appropriate dose and frequency of administration(s) to achieve an optimum clinical result. That is, one of ordinary skill in medicine would be able to administer the appropriate amount of the *Clostridial* toxin, for example botulinum toxin type A, at the appropriate time(s) to effectively treat the eye disorder. The dose of the neurotoxin to be administered depends upon a variety of factors, including the severity of the eye disorder. In some embodiments, the dose of the *Clostridial* toxin administered is effective to treat, e.g. reduce inflammation, of the afflicted eye. The dose of the *Clostridial* toxin s employed in accordance with this invention may be equivalent to the dose of BOTOX® used in accordance with the present invention described herein. In the various methods of the present invention, from about 0.01 U/kg (units of botulinum toxin per kilogram of patient weight) to about 15 U/kg, of a BOTOX®, e.g. botulinum toxin type A, can be administered to the afflicted eye. In some embodiments, about 0.1 U/kg to about 20 U/kg of BOTOX® may be administered to the afflicted eye. Use of from about 0.1 U/kg to about 30 U/kg of a BOTOX®, is within the scope of a method practiced according to the present disclosed invention. In one embodiment, about 0.1 U/kg to about 150 U/kg botulinum toxin, for example type A, may be administered to the eye to treat an eye disorder, e.g., bacterial conjunctivitis, fungal conjunctivitis, viral conjunctivitis, uveitis, keratic precipitates, macular edema, and inflammation response after intra-ocular lens implantation.

In some embodiments, a *Clostridial* toxin, e.g., botulinum toxin type A, is administered to the afflicted eye about every six days to provide for effective treatment of the eye. *Clostridial* toxin, e.g., botulinum toxin type A, may also be administered to the afflicted eye about every two weeks, every three weeks, or more, for example, every month or so.

The mode of administration of the present compositions depends on the form of the composition. For example, if the composition is a solution, drops of the composition may be applied to the eye, e.g., from a conventional eye dropper. In general, the present compositions may be applied to the surface of the eye in substantially the same way as conventional ophthalmic compositions are applied. Such administration of the present compositions does provide substantial and unexpected benefits, as described elsewhere herein.

The present invention also provides compositions for treating an eye disorder in a mammal. In some embodiments, the composition comprises an ophthalmically acceptable carrier, a *Clostridial* toxin in an amount effective to treat an eye disorder when the composition is administered to an eye, and a polyanionic component in an amount effective to provide lubrication to an eye when the composition is administered to an eye. The *Clostridial* toxin may be produced from *Clostridial beratti*, a *Clostridia butyricum*, a *Clostridial tetani* bacterium or a *Clostridial botulinum*. In some embodiments, the composition is a solution. The *Clostridial* toxin s include, but are not limited to, tetanus toxins and botulinum toxin types A, B, $C_1$, D, E, F, G and/or any mixtures thereof.

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex) (available from Allergan, Inc., of Irvine, Calif. under the tradename BOTOX® in 100 unit vials)) is a $LD_{50}$ in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18 to 20 grams each.

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, HC, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype $C_1$ was originally thought to cleave syntaxin, but was found to cleave syntaxin and SNAP-25. Each of the botulinum toxins specifically cleaves a different bond, except botulinum toxin type B (and tetanus toxin) which cleave the same bond.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. A substrate for a botulinum toxin can be found in a variety of different cell types. See e.g. *Biochem*, J 1; 339 (pt 1):159-65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by *Clostridial bacterium* as complexes comprising the 150 kD botulinum toxin protein molecule along with associated non-toxin proteins. Thus, the botulinum toxin type A complex can be produced by *Clostridial bacterium* as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [$^3$H]Noradrenaline and [$^3$H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It is known that botulinum toxin type A can have an efficacy for up to 12 months (*European J. Neurology* 6 (Supp 4): S111-S1150:1999), and in some circumstances for as long as 27 months. *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A botulinum toxin type B preparation (MyoBloc®) is available from Elan Pharmaceuticals of San Francisco, Calif.

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

Acetylcholine

Each type of neuron in the mammalian nervous system may release only a single type or multiple types of neurotransmitters. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

A composition, carrier component or other material is "ophthalmically acceptable" when it is compatible with ocular tissue such that it does not cause significant or undue detrimental effects when brought into contact with ocular tissue. In some embodiments, the ophthalmically acceptable material is also compatible with other components of the present compositions.

In some embodiment, an ophthalmically acceptable carrier comprises water and has a pH in a range of about 6.7 to about 7.4, or about 6.8 to about 7.2. In some embodiment, the carrier component comprises an electrolyte, for example, calcium, magnesium and/or mixtures thereof, in an amount which is ophthalmically acceptable.

In some embodiments, the polyanionic component comprises an anionic cellulosic derivative. For example, the polyanionic component may comprise carboxy methyl celluloses, anionic homopolymers and copolymers comprising units of one or more of acrylic acid, methacrylic acid, metal acrylates and metal methacrylates, and/or mixture thereof. The present compositions may comprise about 0.05% to about 5% (w/v), or 0.3% to about 2% of a polyanionic component.

In some embodiments, the compositions further comprise a vasoconstrictor. Non-limiting examples of vasoconstrictors that may be used in accordance with the present invention include: tetrahydrozoline, ephedrine, naphazoline, phenylephrine, and/or mixtures thereof. In one useful embodiment, the present composition comprises about 0.001% to about 0.5% (w/v), or about 0.005% to about 0.2% (w/v) of the vasoconstrictor.

In some embodiments, the pH of the compositions is about 6 to about 8, about 6.8 to about 7.5, more preferably about 6.8 to about 7.2, or about 7 to about 7.2.

The compositions of the present invention may also include a suitable tonicity adjusting components. In some embodiments, tonicity adjusting components include, but are not limited to, sodium borate, boric acid, sodium chloride, potassium chloride, mannitol, dextrose, glycerin, propylene glycol, and the like and/or mixtures thereof.

The present compositions may be prepared using conventional procedures and techniques, which are well known to the skilled artisan. For example, the present compositions can be prepared by blending the components together, such as in one bulk.

The present compositions may be effectively used, as needed, by methods which comprise administering an effective amount of the compositions to an eye in need of treatment for an eye disorder. The administering step may be repeated as needed to provide effective reduction of inflammation of such eye.

EXAMPLES

Example 1

Method of Treating Bacterial and Fungal Conjunctivitis

Conjunctivitis is an inflammation of the conjunctiva characterized by hyperemia ("red eye"), discharge, foreign-body sensation, and/or stuck eye lids often during sleep. It can be caused by infection of the conjunctiva by bacteria and fungi. A bacteria infection is determined by, for example, colorful discharge, papillae and corneal staining pattern. A fungal infection is determined by, for example, a feathery border at the corneal infection site. Both may be confirmed by culture and sensitivity lab testing. If there is a history of trauma, particularly with vegetable matter (e.g., a tree branch), fungal conjunctivitis is often involved. The following presents a typical treatment protocol that may be carried out for bacterial and fungal conjunctivitis.

A 20-year-old woman presents with a "red eye", foreign-body sensation, and yellowish discharge from the right eye which has lasted for 3 days. She also reports that her lids are stuck together in the morning. This patient is diagnosed with bacterial conjunctivitis in the right eye.

The doctor treats the patient by, for example, topically administering one drop (comprising about 1 unit of a botulinum toxin type A or alternately comprising about 50 units of a botulinum toxin type B) of a composition comprising a *Clostridial* toxin, e.g. botulinum toxin type A. Additionally, the treatment may be supplemented with topical antibiotic drops (e.g. Polytrim 4× a day for 5 to 7 days) at the discretion of the doctor.

If the diagnosis were fungal conjunctivitis, the patient would be treated by topically applying one drop (comprising about 1 unit of a botulinum toxin type A or alternately comprising about 50 units of a botulinum toxin type B) of the present composition. Also, the treatment may be supplemented with topical antifungal drops—5% Natamycin drops every 1-2 hours while awake, and every 2 hours at night.

One week after the application of the *Clostridial* toxin, e.g. botulinum toxin type A, to the afflicted eye, the patient may return to the optometrist for a follow up visit. The patient's condition is improved by at least 50%, such that the inflammation of the eye subsides and the redness is substantially cleared.

Example 2

Method of Treating Viral Conjunctivitis

Viral conjunctivitis tends to occur with a history of a recent upper respiratory tract infection or contact with someone with conjunctivitis. It usually starts in one eye and then involves the other eye a few days later. The viral infection is determined by mild hyperemia (pink eye), excessive tearing, foreign body sensation, follicular conjunctival reaction and may involve lymph node tenderness. The following presents a typical treatment protocol that may be carried out for viral conjunctivitis.

A 34-year-old man presents with a "red eye" that started about 3 days ago in the left eye and then spread to the right eye. The eyes are watery, swollen, and mildly red. He reports having a flu for the past week. This patient is diagnosed with viral conjunctivitis.

The doctor treats the patient by topically administering to the patient's eye one drop (comprising about 1 unit of a botulinum toxin type A or alternately comprising about 50 units of a botulinum toxin type B) of a composition comprising a *Clostridial* toxin, e.g. botulinum toxin type A. Treatment may further include the use of artificial tears, cool compresses and antihistamine drops (if itchiness is severe).

Five days after the application of the composition comprising a *Clostridial* toxin, e.g. botulinum toxin type A, to the afflicted eye, the patient may return to the optometrist for a follow up visit. The patient's condition may be improved by at least 40%, such that the inflammation of the eye subsided and the redness is substantially cleared.

Example 3

Method of Treating Uveitis

Uveitis is a general term referring to inflammation of the uveal tract (iris, ciliary body, and choroid). Although it refers primarily to inflammation of this vascular structure, adjacent structures such as retina, vitreous, sclera, and cornea are also frequently involved. Patients most afflicted are 20-50 years of age, with a marked decrease after the age of 70.

Anterior uveitis (iritis) occurs more frequently than posterior uveitis and affects the iris and/or ciliary body. Anterior uveitis, especially acute uveitis, is usually marked by eye pain, redness, photophobia (light sensitivity), mildly decreased vision, and tearing, and may be unilateral or bilateral depending on the etiology. The critical sign of uveitis is cells and flare (white blood cells and protein leakage) in the anterior chamber. Many cases of acute, non-recurrent, anterior uveitis tend to be idiopathic and are treated primarily with anti-inflammatory/steroid drops. Other causes of acute anterior uveitis (which can be recurrent) include: ocular trauma, post-surgical inflammation, medications, contact lens-related complications, HLA-B27 antigen, and inflammatory/autoimmune conditions (ankylosing spondylitis, inflammatory bowel disease, Reiter's syndrome, etc.) In cases of chronic anterior uveitis, the etiology is usually due to other systemic conditions such as juvenile rheumatoid arthritis, sarcoidosis, herpes simplex/herpes zoster/varicella, tuberculosis, and Fuch's heterochromia iridocyclitis.

Posterior uveitis involves the posterior segment of the eye (with corresponding retinal/choroidal inflammation and lesions). The onset may be acute but most often is insidious with little pain and minimum photophobia and blurred vision. Diseases with associated posterior uveitis include Lyme disease, toxoplasmosis, toxocariasis, histoplasmosis, and syphilis. The following presents a typical treatment protocol that may be carried out for uveitis.

A 25-year-old woman presents with a red and irritated left eye. She reports that it started feeling painful and tearing up 1 day ago, with increased pain when she goes out into bright sunlight. Vision is slightly blurring out of the left eye. Symptoms are reported to be moderate. She reports good health overall, is not taking any medications, and a negative history of trauma. She is diagnosed with a moderate case of acute anterior uveitis/iritis upon exam (presence of cells and flare, conjunctival injection, photophobia), which is probably idiopathic.

The doctor treats the patient by topically administering two drops (comprising about 2 units of a botulinum toxin type A or alternately comprising about 100 units of a botulinum toxin type B) of a composition comprising a *Clostridial* toxin, e.g. botulinum toxin type A. Additionally, if it is deemed necessary, the doctor may supplement the treatment with topical steroid drops (1% prednisolone acetate every 2 hours for 2 days, then taper to 4× a day for 4 days, then 2× a day for 4 more days).

After one week, the patient returns to the doctor's office for a follow up visit. The symptoms of uveitis appears to have subsided. In particular, the inflammation of the uveal tract (iris, ciliary body, and choroid) appears to have subsided by about 50%.

Example 4

Method of Treating Keratic Precipitates

Keratic precipitates are associated with acute or chronic anterior uveitis (inflammation of the uveal tract). In this condition, the critical sign seen in the eyes is cellular infiltrates of lymphocytes and plasma cells (cells and flare) and also the presence of precipitates on the corneal endothelium and/or pupillary border known as keratic precipitates (KPs). Depending on the etiology of the uveitis, KPs can be fine or large. The following presents a typical treatment protocol that may be carried out for KPs.

A 29-year-old man presents with complaints of red eyes and extreme photophobia, onset 2 days ago. Exam reveals presence of moderate cells and flare and a few large KPs along the pupillary border of both eyes. The patient reports a history of Reiter's syndrome and has had recurrent episodes of uveitis in the past 3 years. The patient is diagnosed with acute, anterior chamber uveitis secondary to Reiter's syndrome.

The doctor treats the patient by topically administering one drop of a composition comprising a *Clostridial* toxin, e.g. botulinum toxin type A, to the patient's eye. At the doctor's discretion, she can additionally place the patient on topical steroid drops (1% prednisolone acetate every 1 hour for 1-2 days, then taper). Furthermore, due to the systemic etiology of the uveitis, other treatment options may call for medical and rheumatological consultation.

About 3-4 days after the administration of A *Clostridial* toxin, e.g. botulinum toxin type A, the patient returns the doctor's office for a follow up. The patient shows signs of improvement, with reduced symptoms of photophobia, along with a mild presence of cells and flare, and the keratic precipitates are resolving.

Example 5

Method of Treating Macular Edema (Cystoid Macular Edema)

Retinal edema is characterized by swelling of the retinal tissue due to serous leakage. Typically, retinal edema occurs after any type of ocular surgery (i.e. cataract surgery), and is associated with inflammation. Other etiologies include diabetic retinopathy, uveitis, and age-related macular degeneration. The following presents a typical treatment protocol that may be carried out for macular edema.

A 73-year-old man presents with decreased vision about 6 weeks after cataract surgery with surgical complication of vitreous loss. The patient has been compliant with all post-surgical regimen. Upon retinal exam, the macula appears to be edematous, with the macular tissue being slightly raised in comparison to the surrounding retina. Accordingly, this patient's visual acuities were moderately reduced. This patient is diagnosed with cystoid macular edema.

The doctor treats the patient by topically administering to the patient's eye a composition comprising a *Clostridial* toxin, e.g. about 1 unit of a botulinum toxin type A or alternately about 50 units of a botulinum toxin type B is administered. The doctor may additionally put the patient on topical non-steroidal anti-inflammatory medication (ketorolac 4× a day) for 6 weeks.

Two to three weeks after the administration of A *Clostridial* toxin, e.g. botulinum toxin type A, the patient returns the doctor's office for a follow up. The patient shows signs of improvement. On retinal exam, the macula is flat and the patient is regaining his vision.

Example 6

Method of Treating Inflammation Response After Intra-Ocular Lens Implantation (Cataract Surgery)

Inflammation after ocular surgeries (particularly cataract surgery) can involve the retina, resulting in cystoid macular edema. The incidence increases with surgical complications such as iris prolapse and vitreous loss. The following presents a typical treatment protocol that may be carried out for inflammation response after intra-ocular lens implantation.

A 69-year-old woman presents with decreased vision about 6 weeks after cataract surgery with surgical complication of vitreous loss. The patient has been compliant with all post-surgical regimen. This patient is diagnosed with cystoid macular edema (a condition associated with an inflammatory response).

The doctor treats the patient by topically administering to the patient's eye a formulation comprising A *Clostridial* toxin, e.g. about 1 unit of a botulinum toxin type A or alternately about 50 units of a botulinum toxin type B is administered. The doctor may additionally put the patient on topical non-steroidal anti-inflammatory medication (ketorolac 4× a day) for 6 weeks.

Three weeks after the administration of the *Clostridial* toxin, e.g. botulinum toxin type A, the patient returns the doctor's office for a follow up. The patient shows signs of improvement, including less macular edema and improved vision.

Various references have been cited herein. The disclosures of each these references are incorporated in their entirety herein by reference.

While this invention has been described with respect to various specific examples and embodiments, it is to be understood that the invention is not limited thereto and that it can be variously practiced with the scope of the following claims.

What is claimed is:

1. A method for treating an eye disorder, comprising:
   administering to an eye of a mammal an ophthalmic composition, wherein the ophthalmic composition is a solution and contains an ophthalmically acceptable carrier, a *Clostridial* toxin in an amount effective to treat the eye disorder when the composition is administered to an eye, a polyanionic component in amount effective to provide lubrication to the eye and a vasoconstrictor comprises from about 0.001% (w/v) to about 0.5% (w/v) of the composition, thereby treating the eye disorder.

2. The method of claim 1, wherein *Clostridial* toxin is a botulinum toxin selected from the group consisting of botulinum toxin types A, B, $C_1$, D, E, F, G and mixtures thereof.

3. The method of claim 1, wherein the *Clostridial* toxin is botulinum toxin type A.

4. The method of claim 1, wherein the eye disorder is conjunctivitis.

5. The method of claim 1, wherein the eye disorder is bacterial conjunctivitis, fungal conjunctivitis, viral conjunctivitis, uveitis, keratic precipitates, macular edema, and inflammation response after intra-ocular lens implantation.

6. A method for treating an eye disorder, comprising:
administering to an eye of a mammal an ophthalmic composition, wherein the ophthalmic composition is a solution and contains an ophthalmically acceptable carrier, a *Clostridial* toxin in an amount effective to treat the eye disorder when the composition is administered to an eye, a polyanionic component comprising from about 0.05% (w/v) to about 5% (w/v) of the composition, and a vasoconstrictor, thereby treating the eye disorder.

7. The method of claim 6, wherein *Clostridial* toxin is a botulinum toxin selected from the group consisting of botulinum toxin types A, B, $C_1$, D, E, F, G and mixtures thereof.

8. The method of claim 6, wherein the *Clostridial* toxin is botulinum toxin type A.

9. The method of claim 7, wherein the eye disorder is selected from the group consisting of bacterial conjunctivitis, fungal conjunctivitis, viral conjunctivitis, uveitis, keratic precipitates, macular edema, or inflammation response after intra-ocular lens implantation.

10. The method of claim 7, wherein the ophthalmic composition further comprises a suitable tonicity adjusting component.

11. The method of claim 10, wherein the suitable tonicity adjusting component is selected from the group consisting of sodium borate, boric acid, sodium chloride, potassium chloride, mannitol, dextrose, glycerin, propylene glycol and mixtures thereof.

* * * * *

UNITED STATES PATENT AND TRADEMARK OFFICE
CERTIFICATE OF CORRECTION

PATENT NO. : 7,465,458 B2  Page 1 of 1
APPLICATION NO. : 11/737641
DATED : December 16, 2008
INVENTOR(S) : Eric R. First It is certified that error appears in the above-identified patent and that said Letters Patent is hereby corrected as shown below:

On page 2, in Item (56), under "Other Publications" in column 1, line 14, delete "evealuation" and insert -- evaluation --, therefor.

On page 2, in Item (56), under "Other Publications" in column 2, line 4, delete "Drug" and insert -- Drugs --, therefor.

On page 2, in Item (56), under "Other Publications" in column 2, line 5, delete "Cllinical" and insert -- Clinical --, therefor.

On page 2, in Item (56), under "Other Publications" in column 2, line 9, delete "axiallary" and insert -- axillary --, therefor.

On page 2, in Item (56), under "Other Publications" in column 2, line 33, after "J.M.," insert -- et al., --.

In column 4, line 1, delete "toxin s" and insert -- toxins --, therefor.

In column 5, line 38, delete "toxin s" and insert -- toxins --, therefor.

In column 6, line 13, delete "toxin s" and insert -- toxins --, therefor.

In column 7, line 13, delete "HC," and insert -- $H_C$, --, therefor.

Signed and Sealed this

Tenth Day of March, 2009

JOHN DOLL
*Acting Director of the United States Patent and Trademark Office*